United States Patent [19]

Diana et al.

[11] Patent Number: 5,175,178
[45] Date of Patent: Dec. 29, 1992

[54] 1,2,4-OXADIAZOLYL-PHENOXYALKYLISOXAZOLES AND THEIR USE AS ANTIVIRAL AGENTS

[75] Inventors: Guy D. Diana, Stephentown; Thomas R. Bailey, Bethlehem, both of N.Y.

[73] Assignee: Sterling Drug Inc., New York, N.Y.

[21] Appl. No.: 532,480

[22] Filed: Jun. 4, 1990

Related U.S. Application Data

[63] Continuation-in-part of Ser. No. 396,414, Aug. 21, 1989, Pat. No. 4,942,241.

[51] Int. Cl.⁵ .................. C07D 413/12; A61K 31/41
[52] U.S. Cl. ..................................... 514/364; 548/131
[58] Field of Search ...................... 548/131; 514/364

[56] References Cited

U.S. PATENT DOCUMENTS

| | | | |
|---|---|---|---|
| 4,451,476 | 5/1984 | Diana | 424/272 |
| 4,857,539 | 8/1989 | Diana | 514/378 |

FOREIGN PATENT DOCUMENTS

| | | |
|---|---|---|
| 137242 | 4/1985 | European Pat. Off. |
| 207453 | 1/1987 | European Pat. Off. |

*Primary Examiner*—Robert Gerstl
*Attorney, Agent, or Firm*—Frederik W. Stonner; Paul E. Dupont

[57] ABSTRACT

Compounds of the formulas

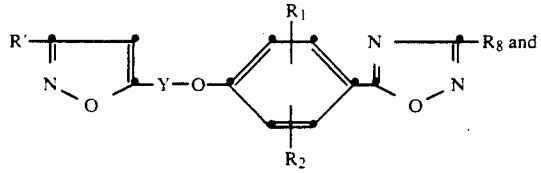

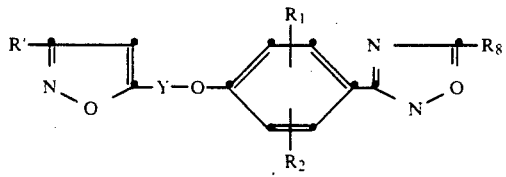

wherein:

Y is an alkylene bridge of 3-9 carbon atoms;

R' is lower-alkyl or hydroxy-lower-alkyl of 1-5 carbon atoms;

$R_1$ and $R_2$ are hydrogen, halogen, lower-alkyl, lower-alkoxy, nitro, lower-alkoxycarbonyl or trifluoromethyl; and $R_8$ is hydrogen or lower-alkyl of 1-5 carbon atoms, with the proviso that when $R_8$ is hydrogen R' is hydroxy-lower-alkyl, are useful as antiviral agents, particularly against picornaviruses, including numerous strains of rhinovirus.

12 Claims, No Drawings

1,2,4-OXADIAZOLYL-PHENOXYALKYLISOX-AZOLES AND THEIR USE AS ANTIVIRAL AGENTS

This application is a continuation-in-part of application Ser. No. 396,414, filed Aug. 21, 1989, now U.S. Pat. No. 4,942,241, issued Jul. 17, 1990.

BACKGROUND OF THE INVENTION a) Field of the Invention

This invention relates to novel heterocyclic substituted-phenoxyalkylisoxazoles and -furans, to methods for the preparation thereof, and compositions and methods for the use thereof as antiviral agents.

b) Information Disclosure Statement

Diana U.S. Pat. No. 4,451,476, issued May 29, 1984, discloses antivirally active compounds having the formula

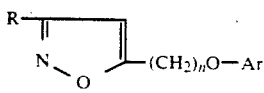

wherein:

R is alkyl of 1 to 3 carbon atoms;

n is an integer from 4 to 8; and

Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

Sterling Drug Inc. European Patent Application Publ. No. 137,242, published Apr. 17, 1985, discloses antivirally active compounds having the formula

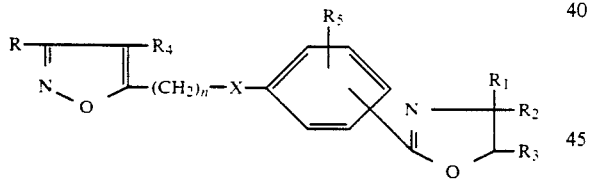

wherein:

R, $R_1$, $R_2$, $R_3$ and $R_4$ are each hydrogen or alkyl of 1 to 3 carbon atoms optionally substituted by hydroxy, lower-alkanoyloxy, lower-alkoxy, chloro, or N=Z, wherein N=Z is amino, lower-alkanoylamino, lower-alkylamino, di-lower-alkylamino, 1-pyrrolidinyl, 1-piperidinyl or 4-morpholinyl; with the proviso that R is other than hydrogen;

$R_5$ is hydrogen, lower-alkyl, halogen, nitro, lower-alkoxy, lower-alkylthio or trifluoromethyl;

X is O or a single bond; and n is an integer from 3 to 9;

and to pharmaceutically acceptable acid-addition salts thereof.

Sterling Drug Inc. European Patent Application Publ. No. 207,453, published Jan. 7, 1987, discloses compounds of Formula I below where Het is 1,3,4-oxadiazol-5-yl, and contemplates compounds where Het is 1,2,4-oxadiazol-5-yl.

SUMMARY OF THE INVENTION

The present invention relates to compounds of the formula

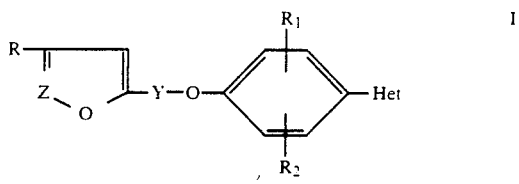

wherein:

Y is an alkylene bridge of 3–9 carbon atoms;

Z is N or HC;

R is hydrogen or lower-alkyl of 1–5 carbon atoms, with the proviso that when Z is N, R is lower-alkyl;

$R_1$ and $R_2$ are hydrogen, halogen, lower-alkyl, lower-alkoxy, nitro, lower-alkoxycarbonyl or trifluoromethyl; and Het is selected from the group consisting of:

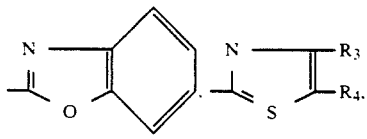

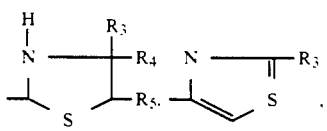

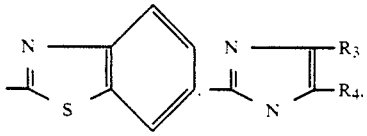

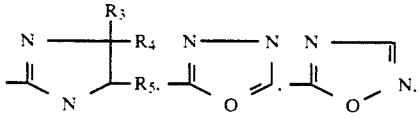

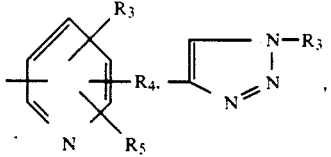

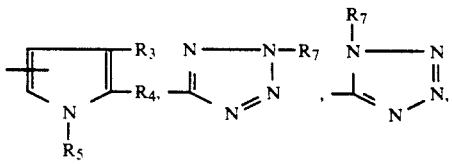

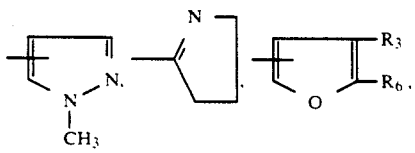

-continued

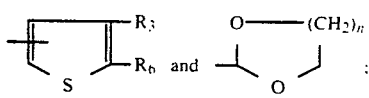

where n is 2 or 3; and

R$_3$, R$_4$ and R$_5$ are hydrogen or lower-alkyl of 1-5 carbon atoms;

R$_6$ is hydrogen, lower-alkyl of 1-5 carbon atoms or chloro;

R$_7$ is hydrogen, or alkyl or hydroxyalkyl of 1-5 carbon atoms;

or pharmaceutically acceptable acid-addition salts of basic members thereof.

A preferred class of compounds within the scope of Formula I are those of the formula

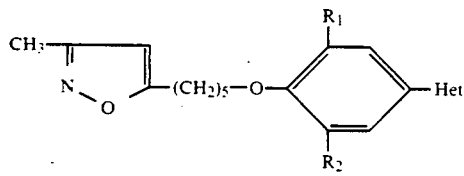 II

The invention also relates to compositions for combating viruses comprising an antivirally effective amount of a compound of Formulas I or II in admixture with a suitable carrier or diluent, and to methods of combating viruses therewith, including the systemic treatment of viral infections in a mammalian host.

DETAILED DESCRIPTION INCLUSIVE OF PREFERRED EMBODIMENTS

The compounds of Formula I where Het is a nitrogen-containing heterocyclic group are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

When the term halogen is used to define the substituents R$_1$ and R$_2$, any of the four common halogens, fluorine, chlorine, bromine or iodine are contemplated; and the term lower-alkoxycarbonyl refers to such groups having from two to four carbon atoms.

The compounds of Formula I can be prepared by a process which comprises reacting a compound of the formula

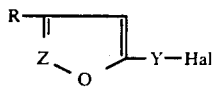 III wherein Hal is chlorine, bromine or iodine, with an alkali metal salt of a compound of the formula

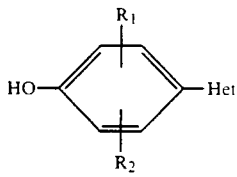 IV

The compounds of Formula I can also be prepared by an alternative process which comprises reacting a compound of the formula

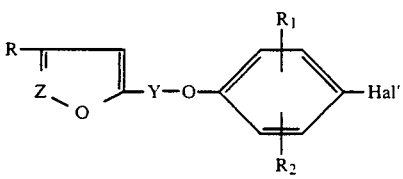 V where Hal' is bromine or iodine, with a compound of the formula (R')$_3$Sn—Het' VI where R' is lower-alkyl of 1-6 carbon atoms, and Het' is any of the aromatic type heterocyclic groups included in the definition of Het in Formula I; in the presence of a palladium complex catalyst.

The process for the preparation of compounds of Formula I by reacting intermediates of Formulas III and IV takes place by heating the reactants in an inert solvent in the presence of an alkali metal base, e.g. potassium carbonate or potassium hydroxide at a temperature between about 50° C. and 150° C.

The intermediates of Formula III where Z is N are prepared by reacting an alkali metal derivative of an isoxazole of the formula

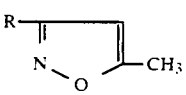 VII with a dihalide, Hal—Y'—Hal, where Y' is an alkylene bridge of 2 to 8 carbon atoms. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula III where Z is HC are prepared from the appropriate omega-(2-furan)alkanoic acid by reduction to the corresponding alcohol and replacement of the hydroxy group by halogen; or by direct alkylation of furan with a dihalide, Hal—Y—Hal, in the presence of a strong base such as butyllithium.

The intermediates of Formula IV are a generically known class of heterocyclic substituted phenols, prepared as described hereinafter in the general description and specific examples.

In the alternative process comprising reacting compounds of Formulas V and VI, the process is carried out using approximately equimolar amounts of the reactants in an inert solvent at a temperature between about 50° C. and 100° C., conveniently at the reflux temperature of the solvent. The reaction is complete in a period ranging from 5-24 hours. The palladium complex catalyst, present to the extent of about 5 mole percent, can be any such catalyst known to effect cross-coupling of organotin compounds with organic halides [cf. Kosugi et al., Bull. Chem. Soc. Japan 59, 677-679 (1986)], for example $PdCl_2(PPh_3)_2$, $Pd(PPh_3)_4$, $PdCl_2[P(o\text{-tolyl})_3]_2$, $PdCl_2 + 2P(OEt)_3$ and $PdCl_2(PhCN)_2$. A preferred catalyst is dichlorobis(triphenylphosphine)palladium $[PdCl_2(PPh_3)_2]$.

The intermediates of Formula V are prepared by reacting an alkali metal salt of a phenol of the formula

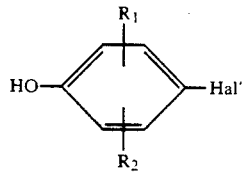

VIII with a compound of Formula III in a procedure analogous to that of the reaction of III with IV.

The organotin reagent of Formula VI is prepared by known procedures comprising reacting a tri-lower-alkyltin halide with an unsubstituted aromatic heterocycle in the presence of a strong base such as butyllithium under anhydrous conditions. The trialkyltin moiety enters the most reactive position on the heterocyclic ring; however, the trialkyltin moiety can be directed to other positions on the heterocyclic ring by using the appropriate halo-substituted heterocycle.

Certain compounds of the invention can be prepared by construction of the Het ring from intermediates having a cyano or formyl group on the phenyl ring, as follows.

The compounds of Formula I where Het is a 4,5-dihydro-1H-imidazolyl group:

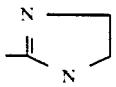

are prepared from the corresponding cyanophenyl compounds of the formula

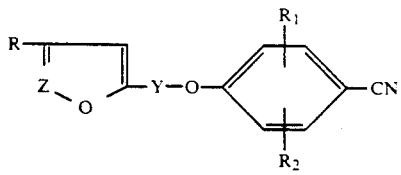

IX by heating the latter with ethylenediamine in acid medium. The compounds of Formula IX are in turn prepared from the appropriate cyanophenol and a compound of Formula III.

The compounds of Formula I where Het is a 2-thiazolyl group:

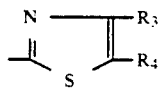

are prepared from the corresponding cyanophenyl compounds of Formula IX by conversion of the latter to the corresponding thioamide with hydrogen sulfide in pyridine, and then reacting the thioamide with a haloalkanone, $R_3CH(Hal)$—$CO$—$R_4$.

The compounds of Formula I where Het is a tetrazole group:

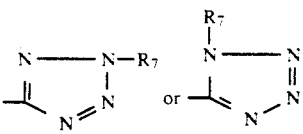

are prepared from the corresponding cyanophenyl compounds of Formula IX by reaction of the latter with sodium azide to give a tetrazole when $R_7$ is hydrogen. Treatment of the latter with a lower-alkyl halide or hydroxy-loweralkyl halide in the presence of a base gives both isomeric tetrazoles where $R_7$ is lower-alkyl or hydroxy-lower-alkyl.

The compounds of Formula I where Het is a group of the formula

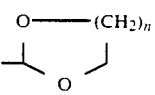

are prepared by conventional cyclic acetal formation by reacting a benzaldehyde derivative of the formula

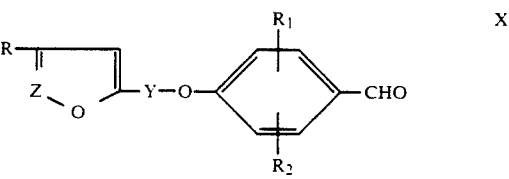

X with ethylene glycol or propylene glycol. The compounds of Formula X are in turn prepared by reacting the appropriate 4-hydroxybenzaldehyde with a compound of Formula III.

The compounds of Formula I where Het is a 2-thiazolidinyl group:

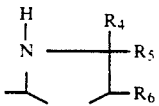

are prepared by reacting a benzaldehyde derivative of Formula X with an amino alkanethiol, $H_2N$—$C(R_4R_5)CH(R_6)$—$SH$, heated in a non-polar organic solvent with an acid catalyst.

The compounds of Formula I where Het is a 4-triazolyl group:

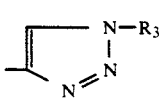

are prepared by reacting a cyanophenyl compound of the Formula IX with the lithium derivative of a N-nitrosoamine, $R_3(CH_3)N$—$N=O$ according to the procedure of Seebach et al., Angew. Chem., International Ed. 11, 1102 (1972).

The compounds of Formula I where Het is a 4,5-dihydro-3H-pyrrol-2-yl group:

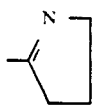

can be prepared by reacting a compound of Formula V with 1-trimethylsilylpyrrolidin-2-one according to the procedure described by Feringa and Jansen, Tetrahedron Letters 507 (1986).

The invention also contemplates compounds of the formulas

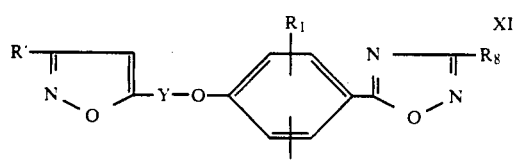

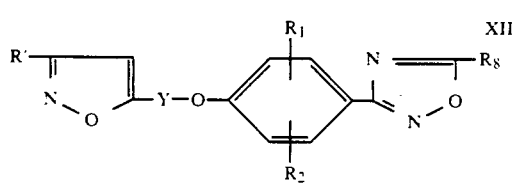

where R' is lower-alkyl or hydroxy-lower-alkyl of 1-5 carbon atoms, $R_8$ is hydrogen or lower-alkyl of 1-5 carbon atoms, and Y, $R_1$ and $R_2$ have the meanings given hereinabove.

The compounds of Formula XI can be prepared by reacting an amide of the formula

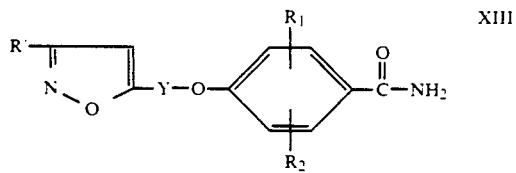

with a compound of the formula $(CH_3)_2N-C(OCH_3)_2-R_8$, followed by reaction of the resulting product with hydroxylamine in acetic acid solution. The amides of Formula XIII are in turn prepared by acid hydrolysis of the corresponding nitrile (see Formula IX).

The compounds of Formula XII can be prepared by reacting a nitrile of Formula IX (R=R', Z=N), or the imino chloride derivative thereof, with hydroxylamine, followed by reaction of the resulting product with an anhydride of the formula $(R_8CO)_2O$.

Alternatively, the compounds of Formulas XI and XII cab be prepared by reacting a compound of one of the formulas:

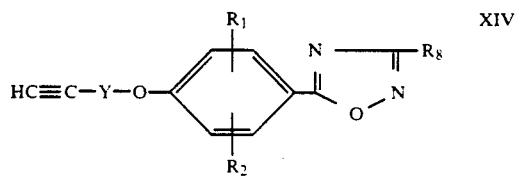

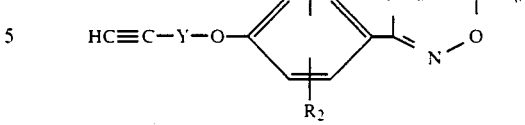

with a 1-nitroalkane ($R'CH_2NO_2$) and phenylisocyanate or with an alkanecarboxaldehyde oxime ($R'CH=NOH$) and N-halosuccinimide where halo is bromo or chloro. The intermediates of Formulas XIV and XV are in turn prepared by procedures described hereinabove and as illustrated in Example 5 below.

The structures of the compounds of the invention were established by the modes of synthesis, by elementary analysis, and by infrared and nuclear magnetic resonance spectra.

The following examples will further illustrate the invention.

EXAMPLE 1

3-Methyl-5-{5-[4-(1,3,4-oxadiazol-2-yl)phenoxy]pentyl}isoxazole

II; $R_1$ and $R_2$=H, Het=2-(1,3,4-oxadiazolyl)

A mixture of 23.6 g 4-(1,3,4-oxadiazolyl)phenol (U.S. Pat. No. 4,218,458, Example XIX), 35 g 5-(5-bromopentyl)-3-methylisoxazole and 40 g milled potassium carbonate in 1.5 liters acetonitrile under nitrogen was heated to reflux. A catalytic amount of sodium iodide was added and refluxing continued for 4 hrs. The reaction mixture was filtered and concentrated to a solid residue. The latter was dissolved in ethyl acetate and the solution washed with water and saturated sodium chloride solution, dried over magnesium sulfate and concentrated in vacuo. The residue was recrystallized from triethylamine to give 18.5 g 3-methyl-5-{5-[4-(1,3,4-oxadiazol-2-yl)phenoxy]pentyl}isoxazole, white needles, m.p. 84°-86° C.

It is further contemplated that 4-(1,2,4-oxadiazol-5-yl)phenol can be caused to react with 5-(5-bromopentyl)-3-methylisoxazole according to the procedure of Example 1 to give 5-{5-[4-(1,2,4-oxadiazol-5-yl)phenoxy]pentyl}-3-methylisoxazole [II; $R_1$ and $R_2$=H, Het=1,2,4-oxadiazol-5-yl].

EXAMPLE 2 a) 3,5-Dimethyl-4-[5-(3-methylisoxazol-5-yl)pentyloxy]benzamide [XIII; Y=$(CH_2)_5$, R'=$CH_3$, $R_1$ and $R_2$=3,5-$(CH_3)_2$]

A solution of 6.3 g 5-[5-(2,6-dimethyl-4-cyanophenoxy)pentyl]-3-methylisoxazole [IX; Z=N, Y=$(CH_2)_5$, R=$CH_3$, $R_1$ and $R_2$=2,6-$(CH_3)_2$; m.p. 50°-51° C.] in 15 ml 97% sulfuric acid was stirred at room temperature for 1.5 hours. The reaction mixture was poured onto ice and extracted with ethyl acetate. The organic layer was washed with water, dried over sodium sulfate and concentrated in vacuo. The residue was recrystallized from isopropyl acetate-hexane and used directly in the next reaction.

b) 5-{5-[2,6-Dimethyl-4-(3-methyl-1,2,4-oxadiazol-5-yl)phenoxy]pentyl}-3-methylisoxazole [XI; Y=$(CH_2)_5$, R'=$CH_3$, $R_1$ and $R_2$=2,6-$(CH_3)_2$, $R_8$=$CH_3$]

A suspension of 2.7 g of the product of part (a) in 15 ml dimethylacetamide dimethyl acetal was heated at reflux under nitrogen for two hours. The reaction mixture was concentrated in vacuo and then treated with 0.7 g hydroxylamine hydrochloride, 2.0 ml 5N sodium hydroxide solution and 7.5 ml 70% aqueous acetic acid. The resulting mixture was stirred for 30 min. and then 4.5 ml water was added. The reaction mixture was extracted with ethyl acetate, and the organic layer was washed with water, dried over sodium sulfate and concentrated in vacuo. The residue was subjected to flash filtration (silica gel; 1:1 hexane/ethyl acetate), and chromatography (MPLC, silica gel 60; 3:1 hexane/ethyl acetate) to give 2.4 g (80%) of 5-{5-[2,6-dimethyl-4-(3-methyl-1,2,4-oxadiazol-5-yl)phenoxy]pentyl}-3-methylisoxazole, m.p. 54°–56° C. when crystallized from isopropyl acetate/hexane.

EXAMPLE 3 a) 3,5-Dimethyl-4-[3-(3-methylisoxazol-5-yl)propyloxy]benzamide [XIII; $Y=(CH_2)_3$, $R'=CH_3$, $R_1$ and $R_2=3,5-(CH_3)_2$] was prepared from 6 g 5-[3-(2,6-dimethyl-4-cyanophenoxy)propyl]-3-methylisoxazole [IX; $Z=N$, $Y=(CH_2)_3$, $R=CH_3$, $R_1$ and $R_2=2,6-(CH_3)_2$; m.p. 46°–48° C. when recrystallized from methanol] according to the procedure of Example 2, part (a), and was obtained in 65% yield in the form of a colorless solid, m.p. 162°–163° C. when recrystallized from methanol.

b) 5-{3-[2,6-Dimethyl-4-(3-methyl-1,2,4-oxadiazol-5-yl)phenoxy]propyl}-3-methylisoxazole [XI; $Y=(CH_2)_3$, $R'=CH_3$, $R_1$ and $R_2=2,6-(CH_3)_2$, $R_8=CH_3$] was prepared from 6 g of the product of part (a), 30 g dimethylacetamide dimethyl acetal and 1.75 g hydroxylamine hydrochloride according to the procedure of Example 1, part (b), and was obtained (1.7 g) in the form of a colorless solid, m.p. 55.5°–56.5° C. when recrystallized from isopropyl acetate-hexane.

It is contemplated that, according to the foregoing procedures, 5-[5-(2,6-dimethyl-4-cyanophenoxy)pentyl]-3-hydroxymethylisoxazole (yellowish-tan solid, m.p. 63°–64° C. from diethyl ether) can be converted to 3,5-dimethyl-4-[5-(3-hydroxymethylisoxazol-5-yl)pentyloxy]benzamide [XIII; $Y=(CH_2)_5$, $R'=HOCH_2$, $R_1$ and $R_2=3,5-(CH_3)_2$] and the latter converted to 5-{5-[2,6-dimethyl-4-(3-methyl-1,2,4-oxadiazol-5-yl)phenoxy]pentyl}-3-hydroxymethylisoxazole [XI; $Y=(CH_2)_5$, $R'=HOCH_2$, $R_1$ and $R_2=2,6-(CH_3)_2$, $R_8=CH_3$]. The intermediate nitrile was prepared from 2,6-dimethyl-4-cyanophenol and 5-(5-chloropentyl)-5-hydroxymethylisoxazole, the latter in turn prepared by reacting 1-bromo-4-chlorobutane with 3-hydroxymethyl-5-methylisoxazole in the presence of n-butyllithium. The 3-hydroxymethyl-5-methylisoxazole (b.p. 77°–80° C., 0.5 mm) was in turn prepared by reduction of methyl 5-methylisoxazole-3-carboxylate with lithium aluminum hydride.

Similarly, it is contemplated that 5-[5-(2,6-dichloro-4-cyanophenoxy)pentyl]-3-methylisoxazole (m.p. 59°–60° C.) can be converted to 5-{5-[2,6-dichloro-4-(3-methyl-1,2,4-oxadiazol-5-yl)phenoxy]pentyl}-3-methylisoxazole [XI; $Y=(CH_2)_5$, $R'=CH_3$, $R_1$ and $R_2=2,6-Cl_2$, $R_8=CH_3$].

EXAMPLE 4 a) 5-(3-Chloropropyl)-3-ethylisoxazole

A mixture of 11.56 g 1-nitropropane, 15 g 1-chloro-4-pentyne [$HC\equiv C(CH_2)_3Cl$], 37 g phenylisocyanate and 4 ml triethylamine in 300 ml toluene was stirred at room temperature for three days. The reaction mixture was filtered, the filtrate concentrated in vacuo, and the residue chromatographed (silica gel, eluted with hexane and 20% ethyl acetate in hexane) to give 12 g 5-(2-chloropropyl)-3-ethylisoxazole as a yellow oil.

b) 5-[3-(2,6-Dimethyl-4-cyanophenoxy)propyl]-3-ethylisoxazole [IX; $Z=N$, $Y=(CH_2)_3$, $R=C_2H_5$, $R_1$ and $R_2=2,6-(CH_3)_2$]

To a mixture of 7.84 g 4-cyano-2,6-dimethylphenol, 3.57 g potassium hydroxide and 10.6 g potassium iodide in 200 ml acetonitrile was added 12 g 5-(2-chloropropyl)-3-ethylisoxazole, and the mixture was heated at reflux for about 16 hrs. The reaction mixture was concentrated in vacuo and the residue partitioned between ethyl acetate and water. The ethyl acetate layer was washed with aqueous sodium hydroxide (10%) until the excess starting phenol was removed, and the solution concentrated to give 10 g of 5-[3-(2,6-dimethyl-4-cyanophenoxy)propyl]-3-ethylisoxazole as a yellow oil. A sample of the latter was obtained in crystalline form, m.p. 50°–51° C. by crystallization from methanol at −50° C.

c) 3,5-Dimethyl-4-[3-(3-ethylisoxazol-5-yl)propyloxy]benzamide [XIII; $Y=(CH_2)_3$, $R'=C_2H_5$, $R_1$ and $R_2=3,5-(CH_3)_2$] was prepared from the product of part (b) (10 g) by the procedure of Example 2, part (a) and was obtained (8.7 g) as a solid, m.p. 132°–134° C. when washed with ethyl acetate.

d) 5-{3-[2,6-Dimethyl-4-(3-methyl-1,2,4-oxadiazol-5-yl)phenoxy]propyl}-3-ethylisoxazole [XI; $Y=(CH_2)_3$, $R'=C_2H_5$, $R_1$ and $R_2=2,6-(CH_3)_2$, $R_8=CH_3$] was prepared from 4.15 g of the product of part (c), 20.5 g dimethylacetamide dimethyl acetal and 1.2 g hydroxylamine hydrochloride according to the procedure of Example 1, part (b), and was obtained (2.1 g) in the form of a colorless solid, m.p. 40°–41° C. when recrystallized from isopropyl acetate/hexane.

EXAMPLE 5 a) Ethyl 3,5-dimethyl-4-(3-ethynylpropoxy)benzoate

A suspension of 6.42 g ethyl 3,5-dimethyl-4-hydroxybenzoate, 5.5 g potassium iodide, 3.7 g 1-chloro-4-pentyne and 2.3 g powdered potassium hydroxide in 650 ml acetonitrile was heated at reflux under nitrogen for 16 hrs. The mixture was filtered, concentrated in vacuo and subjected to flash filtration (silica gel, 4:1 hexane/ethyl acetate) to give 7.4 g ethyl 3,5-dimethyl-4-(3-ethynylpropoxy)benzoate as a yellow oil.

b) 3,5-Dimethyl-4-(3-ethynylpropoxy)benzoic acid

The ethyl ester of part (a) (7.4 g) was hydrolyzed, first with 0.9 g lithium hydroxide in 25 ml methanol and 10 ml water, stirred at room temperature for 3 days, and then with 50 ml 10% sodium hydroxide in 100 ml ethanol, heated at reflux for 2 hrs. The product was isolated by acidification, extraction with ether and concentration to give 4.7 g 3,5-dimethyl-4-(3-ethynylpropoxy)benzoic acid, m.p. 129°–130° C.

c) 3,5-Dimethyl-4-(3-ethynylpropoxy)benzamide

To a solution of 4.7 g 3,5-dimethyl-4-(3-ethynylpropoxy)benzoic acid in 100 ml dry tetrahydrofuran was added 3.7 g carbonyldiimidazole and the mixture was stirred 2 hrs. at room temperature. To the latter was added 10 ml concentrated ammonium hydroxide, and the mixture was stirred for 30 min., poured onto water and extracted with ethyl acetate. The organic layer was dried (MgSO$_4$), filtered and concentrated to give 4.7 g 3,5-dimethyl-4-(3-ethynylpropoxy)benzamide, m.p. 81°–84° C.

d) 5-[3,5-Dimethyl-4-(3-ethynylpropoxy)phenyl]-3-methyl-1,2,4-oxadiazole [XIV; $Y=(CH_2)_3$, $R_1$ and $R_2=3,5-(CH_3)_2$, $R_8=CH_3$] was prepared from 4.7 g 3,5-dimethyl-4-(3-ethynylpropoxy)benzamide, 31 ml dimethylacetamide dimethyl acetal and 1.7 g hydroxylamine hydrochloride according to the procedure of Example 2, part (b), and was obtained (4.4 g) in the form of a viscous oil used directly in the next reaction. A sample when crystallized from isopropyl acetate/hexane had the m.p. 38°-40° C.

e) 5-{3-[2,6-Dimethyl-4-(3-methyl-1,2,4-oxadiazol-5-yl)phenoxy]propyl}-3-(n-propyl)isoxazole [XI; $Y=(CH_2)_3$, $R'=CH_3CH_2CH_2$, $R_1$ and $R_2=2,6-(CH_3)_2$, $R_8=CH_3$]

To a solution of 4.4 g of the product of part (d), 1.7 g 1-nitrobutane and 12 drops triethylamine in 40 ml dry toluene was added a solution of 3.7 ml phenylisocyanate in 5 ml dry toluene dropwise over a 2 hr. period. The reaction mixture was stirred at room temperature for five days under nitrogen, then filtered, concentrated and subjected to chromatography (MPLC, silica gel, 3:1 hexane/ethyl acetate). A first fraction brought out 1.2 g of starting material of part (d), and a second fraction 3.0 g of the desired product which was recrystallized from isopropyl acetate/hexane at −50° C. to give 2.5 g 5-{3-[2,6-dimethyl-4-(3-methyl-1,2,4-oxadiazol-5-yl)phenoxy]propyl}-3-(n-propyl)isoxazole, m.p. 35°-37° C.

EXAMPLE 6

5-{5-[2,6-Dimethyl-4-(5-methyl-1,2,4-oxadiazol-3-yl)phenoxy]pentyl}-3-methylisoxazole XII; $Y=(CH_2)_5$, $R'=CH_3$, $R_1$ and $R_2=2,6-(CH_3)_2$, $R_8=CH_3$ A suspension of 7.0 g 5-[5-(2,6-dimethyl-4-cyanophenoxy)pentyl]-3-methylisoxazole, 1.8 g hydroxylamine hydrochloride and 3.5 g sodium acetate trihydrate in 40 ml 95% ethanol was heated at reflux under nitrogen for two days. The reaction mixture was filtered, concentrated in vacuo, and the residue in 50 ml acetic anhydride was heated at reflux for 3 hrs. The reaction mixture was poured over ice/10% sodium hydroxide and extracted with ether. The ether extracts were washed with water and saturated sodium bicarbonate, dried ($K_2CO_3$), concentrated and subjected to flash filtration (silica gel 60, 3:1 hexane/ethyl acetate) followed by chromatography (MPLC, silica gel 60, 3:1 hexane/ethyl acetate). The resulting product was crystallized from isopropyl acetate/hexane to give 2.7 g 5-{5-[2,6-dimethyl-4-(5-methyl-1,2,4-oxadiazol-3-yl)phenoxy]pentyl}-3-methylisoxazole, m.p. 45°-46° C.

Similarly, it is contemplated that 5-[5-(2,6-dimethyl-4-cyanophenoxy)pentyl]-3-hydoxymethylisoxazole or 5-[5-(2,6-dichloro-4-cyanophenoxy)pentyl]-3-methylisoxazole can be converted, respectively, to 5-{5-[2,6-dimethyl-4-(5-methyl-1,2,4-oxadiazol-3-yl)phenoxy]pentyl}-3-hydroxymethylisoxazole [XII; $Y=(CH_2)_5$, $R'=HOCH_2$, $R_1$ and $R_2=2,6-(CH_3)_2$, $R_8=CH_3$], or 5-{5-[2,6-dichloro-4-(5-methyl-1,2,4-oxadiazol-3-yl)phenoxy]pentyl}-3-methylisoxazole [XII; $Y=(CH_2)_5$, $R'=CH_3$, $R_1$ and $R_2=2,6-Cl_2$, $R_8=CH_3$]

EXAMPLE 7

5-{3-[2,6-Dimethyl-4-(5-methyl-1,2,4-oxadiazol-3-yl)phenoxy]propyl}-3-methylisoxazole [XII; $Y=(CH_2)_3$, $R'=CH_3$, $R_1$ and $R_2=2,6-(CH_3)_2$, $R_8=CH_3$] was prepared from 6 g of the imino chloride derived by reaction of 5-[3-(2,6-dimethyl-4-cyanophenoxy)propyl]-3-methylisoxazole with ethanolic hydrogen chloride, 1.49 g of hydroxylamine hydrochloride and 100 ml acetic anhydride according to the procedure of Example 6, and was obtained (4 g) as a colorless solid, m.p. 80°-82° C. when recrystallized from methanol.

EXAMPLE 8 a) 3,5-Dimethyl-4-(3-ethynylpropoxy)benzonitrile

A mixture of 40 g 3,5-dimethyl-4-hydroxybenzonitrile, 30.77 g 1-chloro-4-pentyne, 74.63 g potassium carbonate and 130 ml N-methylpyrrolidinone was heated with stirring to 100° C. and stirring was continued at 100° C. for 4 hrs. The mixture was cooled to room temperature and 800 ml of water was added. This mixture was extracted with 400 ml ethyl acetate and the extract was washed with 2N sodium hydroxide and saturated sodium chloride solution, dried over anhydrous magnesium sulfate and concentrated in vacuo. The resulting black oil, dissolved in ethyl acetate, was passed through a pad of florisil to remove the color and the filtrate was concentrated in vacuo. The residue was recrystallized from methyl alcohol to yield 34.64 g (60.2%) of 3,5-dimethyl-4-(3-ethynylpropoxy)benzonitrile, m.p. 48°-49° C.

b) 3-[3,5-Dimethyl-4-(3-ethynylpropoxy)phenyl]-5-methyl-1,2,4-oxadiazole

A mixture of 25 g of the benzonitrile of part (a), 16.6 g of hydroxylamine hydrochloride, 32.64 g sodium acetate trihydrate, 200 ml ethyl alcohol and 40 ml water was refluxed for 5 hrs and cooled to room temperature. The ethyl alcohol was distilled off in vacuo and the residue, after standing overnight at room temperature, was suspended in 200 ml acetic anhydride and the mixture was refluxed for 2 hrs and allowed to cool to room temperature Sodium hydroxide (2N) was added slowly with stirring and ice bath cooling during which time heat and gas were evolved. The mixture was extracted with ether and the extract was washed successively with dilute sodium hydroxide solution, dilute sodium bicarbonate solution and saturated salt solution. The extract was dried over anhydrous sodium sulfate and concentrated in vacuo to a brown oil. A solution of the oil in ethyl acetate was passed through a column of florisil to remove color and concentrated in vacuo. The residue was subjected to chromatography (MPLC, silica gel, 15:85 ethyl acetate/hexane) to give 17.8 g (56%) of 3-[3,5-dimethyl-4-(3-ethynylpropoxy)phenyl]-5-methyl-1,2,4-oxadiazole as a white solid, m.p. 41.5°-43.0° C.

c) 5-{3-[2,6-Dimethyl-4-(5-methyl-1,2,4-oxadiazol-3-yl)phenoxy]propyl}-3-ethylisoxazole [XII; $Y=(CH_2)_3$, $R'=CH_3CH_2$, $R_1$ and $R_2=2,6-(CH_3)_2$, $R_8=CH_3$]

A mixture of 3.99 g N-chlorosuccinimide, 2 drops pyridine and 75 ml N-methylpyrrolidinone was stirred at room temperature until clear and 2.19 g propionaldehyde oxime was added over 10 minutes. Stirring was continued for ½ hour at room temperature and 2.7 g of the 1,2,4-oxadiazole of part (b) in 15 ml N-methylpyrrolidinone was added in one portion. The mixture was heated to 90° C., 4.2 ml triethylamine were added over 3 hrs and stirring and heating were continued for 1 hr. The mixture was cooled to room temperature, suspended in water and extracted with methylene chloride. The extract was washed with water and saturated salt solution, dried over anhydrous magnesium sulfate and concentrated in vacuo. The residue was subjected to chromatography (MPLC, silica gel, 35:65 ethyl acetate/hexane) to give 1.86 g (55%) of 5-{3-[2,6-dimethyl-4-

(5-methyl-1,2,4-oxadiazol-3-yl)phenoxy]propyl}-3-ethylisoxazole as a white solid. m.p. 85°–86° C. after recrystallization from methyl alcohol.

EXAMPLE 9

5-{3-[2,6-Dimethyl-4-(5-methyl-1,2,4-oxadiazol-3-yl)phenoxy]propyl}-3-propylisoxazole XII; $Y=(CH_2)_3$, $R'=CH_3CH_2CH_2$, $R_1$ and $R_2=2,6-(CH_3)_2$, $R_8=CH_3$ Following a procedure similar to that of Example 8(c) but substituting 2.6 g butyraldehyde oxime for the propionaldehyde oxime and using 3.99 g N-chlorosuccinimide, 2 drops pyridine, 50 ml N-methylpyrrolidinone, 2.7 g of the 1,2,4-oxadiazole of part (b) of Example 8 and 4.2 ml triethylamine, there was obtained after chromatography (MPLC, silica gel, 30:70 ethyl acetate/hexane) 2.06 g (58%) of the title compound as white needles, m.p. 69.0°–70.0° C. when recrystallized from methyl alcohol.

Biological evaluation of compounds of Formulas I and II has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Wisconsin) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, $-1A$, $-1B$, $-6$, $-14$, $-21$, $-22$, $-15$, $-25$, $-30$, $-50$, $-67$, $-89$, $-86$ and $-41$. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention. For some of the compounds, the $MIC_{50}$ and $MIC_{80}$ values are based on the testing of fewer than 15 rhinovirus serotypes. In these cases the number of serotypes (N) is indicated in parentheses after the $MIC_{80}$ figure.

| Example No. | $MIC_{50}$ (Rhinovirus) | $MIC_{80}$ (N) (Rhinovirus) |
|---|---|---|
| 2 (b) | 0.053 | 0.42 (6) |
| 3 (b) | 0.026 | 0.12 (15) |
| 4 (d) | 0.042 | 0.15 (15) |
| 5 (e) | 0.036 | 0.06 (7) |
| 6 | 0.018 | 0.10 (5) |
| 7 | 0.012 | 0.069 (13) |
| 8 (c) | 0.017 | 0.05 (6) |

| Example No. | $MIC_{50}$ (Rhinovirus) | $MIC_{80}$ (N) (Rhinovirus) |
|---|---|---|
| 9 | 0.025 | 0.04 (6) |

The antiviral compositions are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration.

We claim:

1. A compound of the formula

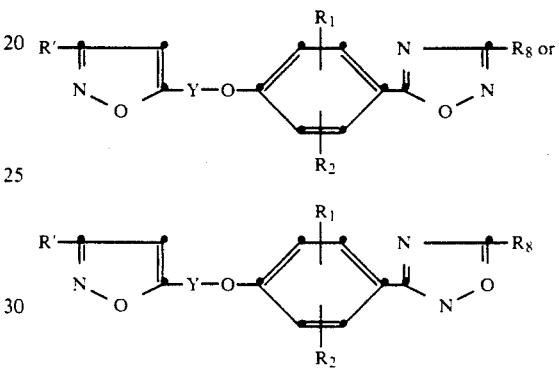

wherein:

Y is an alkylene bridge of 3–9 carbon atoms;

R' is lower-alkyl or hydroxy-lower-alkyl of 1–5 carbon atoms;

$R_1$ and $R_2$ are hydrogen, halogen, lower-alkyl, lower-alkoxy, nitro, lower-alkoxycarbonyl or trifluoromethyl; and $R_8$ is hydrogen or lower-alkyl of 1–5 carbon atoms, with the proviso that when $R_8$ is hydrogen R' is hydroxy-lower-alkyl;

or pharmaceutically acceptable acid-addition salts thereof.

2. A compound according to claim 1 of the formula

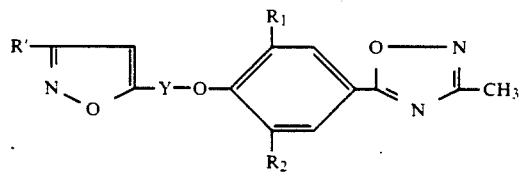

wherein Y is an alkylene bridge of 3–9 carbon atoms; R' is lower-alkyl of 1–5 carbon atoms; and $R_1$ and $R_2$ are hydrogen, halogen or lower-alkyl.

3. 5-{5-[2,6-Dimethyl-4-(3-methyl-1,2,4-oxadiazol-5-yl)phenoxy]pentyl}-3-methylisoxazole, according to claim 2.

4. 5-{3-[2,6-Dimethyl-4-(3-methyl-1,2,4-oxadiazol-5-yl)phenoxy]propyl}-3-methylisoxazole, according to claim 2.

5. 5-{3-[2,6-Dimethyl-4-(3-methyl-1,2,4-oxadiazol-5-yl)phenoxy]propyl}-3-ethylisoxazole, according to claim 2.

6. 5-{3-[2,6-Dimethyl-4-(3-methyl-1,2,4-oxadiazol-5-yl)phenoxy]propyl}-3-propylisoxazole, according to claim 2.

7. A compound according to claim 1 of the formula

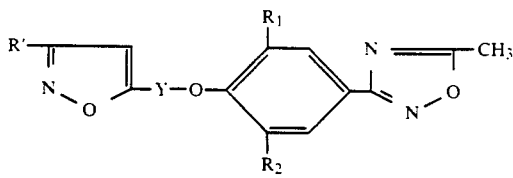

wherein Y is an alkylene bridge of 3-9 carbon atoms; R' is lower-alkyl of 1-5 carbon atoms; and $R_1$ and $R_2$ are hydrogen, halogen or lower-alkyl.

8. 5-{5-[2,6-Dimethyl-4-(5-methyl-1,2,4-oxadiazol-3-yl)phenoxy]pentyl}-3-methylisoxazole, according to claim 7.

9. 5-{3-[2,6-Dimethyl-4-(5-methyl-1,2,4-oxadiazol-3-yl)phenoxy]propyl}-3-methylisoxazole, according to claim 7.

10. 5-{3-[2,6-Dimethyl-4-(5-methyl-1,2,4-oxadiazol-3-yl)phenoxy]propyl}-3-ethylisoxazole, according to claim 7.

11. A composition for combating picornaviruses which comprises an antivirally effective amount of a compound according to claim 1, in admixture with a suitable carrier or diluent.

12. A composition according to claim 11 for combating rhinoviruses.

* * * * *